(12) United States Patent
Warenius

(10) Patent No.: US 12,570,697 B2
(45) Date of Patent: Mar. 10, 2026

(54) CYCLIC PEPTIDE USEFUL IN THE TREATMENT OF CANCER

(71) Applicant: Hilmar M. Warenius, Hitchin (GB)

(72) Inventor: Hilmar M. Warenius, Hitchin (GB)

(73) Assignee: Syntherix Limited, Cambridge (GB)

( * ) Notice: Subject to any disclaimer, the term of this patent is extended or adjusted under 35 U.S.C. 154(b) by 1033 days.

(21) Appl. No.: 17/442,609

(22) PCT Filed: Mar. 25, 2020

(86) PCT No.: PCT/GB2020/050804
§ 371 (c)(1),
(2) Date: Sep. 24, 2021

(87) PCT Pub. No.: WO2020/193978
PCT Pub. Date: Oct. 1, 2020

(65) Prior Publication Data
US 2022/0242914 A1 Aug. 4, 2022

(30) Foreign Application Priority Data
Mar. 25, 2019 (GB) ...................................... 1904099

(51) Int. Cl.
C07K 7/64 (2006.01)
A61K 31/12 (2006.01)
A61P 35/00 (2006.01)

(52) U.S. Cl.
CPC ............... *C07K 7/64* (2013.01); *A61K 31/12* (2013.01); *A61P 35/00* (2018.01)

(58) Field of Classification Search
CPC .......... C07K 7/64; A61K 31/12; A61K 38/00; A61K 38/12; A61P 35/00; C12N 9/12; C12Y 207/11022
See application file for complete search history.

(56) References Cited

U.S. PATENT DOCUMENTS 8,883,718 B2 * 11/2014 Warenius ............. C12N 9/1205
514/1.2

FOREIGN PATENT DOCUMENTS

| WO | 2004/077062 A2 | 9/2004 |
| WO | 2005/123760 A2 | 12/2005 |
| WO | 2009/112536 A1 | 9/2009 |
| WO | 2016/020437 A1 | 2/2016 |
| WO | 2017/137761 A1 | 8/2017 |

OTHER PUBLICATIONS

Bowie et al (Science, 1990, 247:1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*

Guy, Andrew, Office Action, The United Kingdom Patent Office, Application No. GB1904099.7, Mar. 9, 2023.
Romasiyud, Jariya, "Synthesis of the Small Peptide Analogues of Cyclin Dependent Kinase (CDK4) for Cancer Treatment", May 1, 2010, 242 pages.
Schmidt, Yodlee, H., International Search Report and Written Opinion, PCT/GB2020/050804, International Searching Authority, European Patent Office, Sep. 22, 2020.
Warenius, Hilmar M, "Selective anticancer activity of a hexapeptide with sequence homology to a non-kinase domain of Cyclin Dependent Kinase 4", Molecular Cancer, vol. 10, No. 3, Jun. 13, 2011, pp. 1-17.
Classon et al., "The retinoblastoma tumour suppressor in development and cancer", Nat. Rev. Cancer, Dec. 2002, vol. 2, pp. 910-917.
De Marval et al., "Lack of Cyclin-Dependent Kinase 4 Inhibits c-myc Tumorigenic Activities in Epithelial Tissues", Molecular and Cell Biology, Sep. 2004, vol. 24, No. 17, pp. 7538-7547.
Evan et al., "Proliferation, cell cycle and apoptosis in cancer", Nature, May 17, 2001, vol. 411, pp. 342-348.
Gerlinger et al., "Intratumor Heterogeneity and Branched Evolution Revealed by Multiregion Sequencing", The New England Journal of Medicine, Mar. 8, 2012, vol. 366, No. 10, pp. 883-892.
Greenman et al., "Patterns of somatic mutation in human cancer genomes", Nature, Mar. 8, 2007, 446 (7132):153-158.
Harbour et al., "Cdk Phosphorylation Triggers Sequential Intramolecular Interactions that Progressively Block Rb Functions as Cells Move through G1", Cell, Sep. 17, 1999, vol. 98, pp. 859-869.
Jones et al., "Core Signaling Pathways in Human Pancreatic Cancers Revealed by Global Genomic Analyses", Science, Sep. 26, 2008, 321(5897):1801-1806.
Kaufmann et al., "Specific Proteolytic Cleavage of Poly(ADP-ribose) Polymerase: An Early Marker of Chemotherapy-induced Apoptosis", Cancer Research, Sep. 1, 1993, 53, pp. 3976-3985.
Lowe et al., "Apoptosis in cancer", Carcinogenesis, Mar. 2000, vol. 21, Issue 3, pp. 485-495.

(Continued)

*Primary Examiner* — Sudhakar Katakam
(74) *Attorney, Agent, or Firm* — Gavrilovich, Dodd & Lindsey LLP

(57) ABSTRACT

The present invention relates to a cyclic peptide comprising an active region comprising the amino acid sequence $X^1X^2X^3X^4X^5X^6$ or a salt, derivative, prodrug or mimetic thereof. $X^2$ and $X^5$ are arginine; and either:

Figure 1:
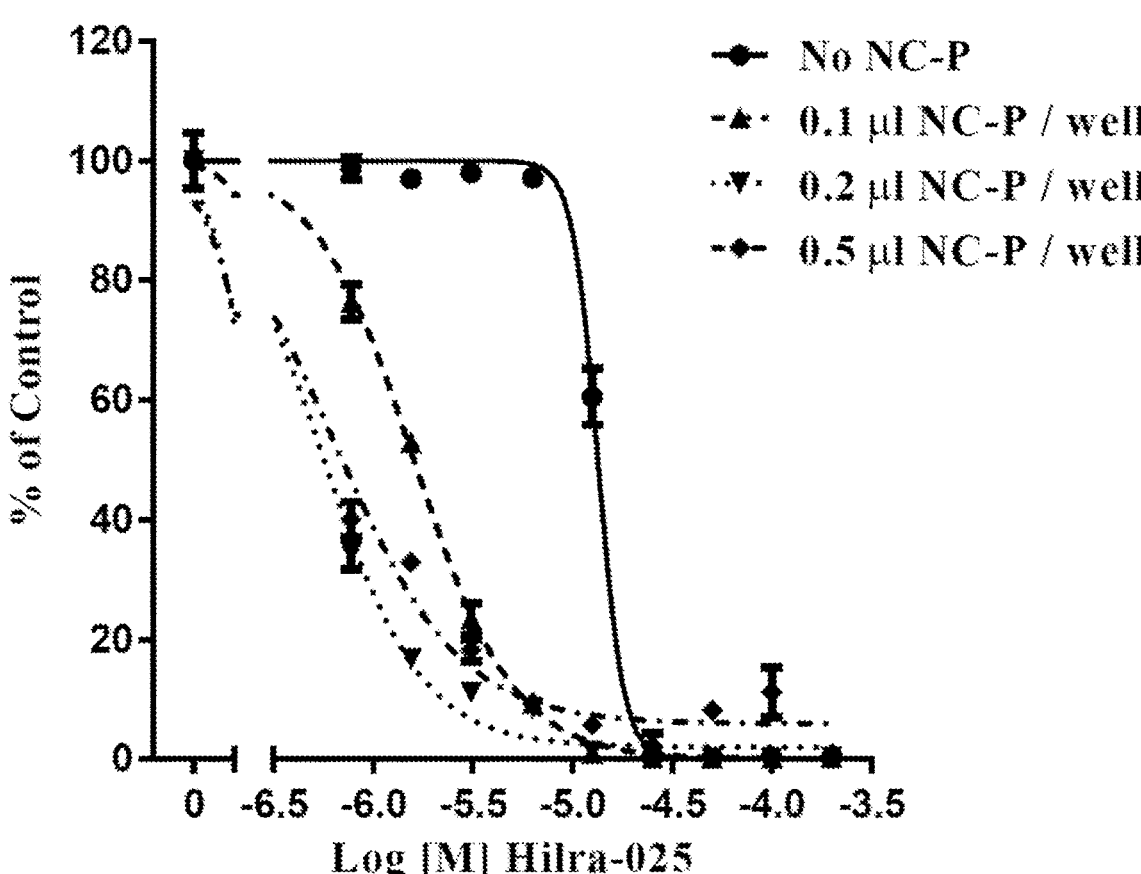

$X^1$ is (7-methoxy-coumarin-4-yl)-Ala-OH (Dac) and $X^3$, $X^4$ and $X^6$ are any amino acid; or $X^3$ is sarcosine (Sar) and $X^1$, $X^4$ and $X^6$ are any amino acid; or $X^4$ is 5,5-dimethylproline (dmPro) or 3-amino-3-(2-naphthyl)propionic acid (Nap) and $X^1$, $X^3$ and $X^6$ are any amino acid; or $X^6$ is Nap and $X^1$, $X^3$ and $X^4$ are any amino acid.

The present invention further relates to a pharmaceutical composition comprising the cyclic peptide and the peptide for use in medicine, and particularly cancer.

14 Claims, 6 Drawing Sheets
Specification includes a Sequence Listing.

(56)                    References Cited

OTHER PUBLICATIONS

Macias et al., "Cdk2 deficiency decrease ras/cdk4-depedent malignant progression, but not myc-induced tumorigenesis", Cancer Res., Oct. 15, 2007, 67(20):9713-9720.

Macias et al., "CDK2 Activation in Mouse Epidermis Induces Keratinocyte Proliferation but Does Not Affect Skin Tumor Development", The American Journal of Pathology, Aug. 2008, vol. 173, No. 2, pp. 526-535.

Nevins et al., "The Rb-E2F pathway and cancer", Human Molecular Genetics, Apr. 1, 2001, vol. 10, No. 7, pp. 699-703.

Ossovskaya et al., "Upregulation of Poly (ADP-Ribose) Polymerase-1 (PARP 1) in Triple-Negative Breast Cancer and Other Primary Human Tumor Types", Genes & Cancer, Oct. 7, 2010, 1(8):812-821.

Qin et al., "Deregulated transcription factor E2F-1 expression leads to S-phase entry and p53-mediated apoptosis", Proc. Natl. Acad. Sci., Nov. 1994, vol. 91, pp. 10918-10922.

Rodriguez-Puebla et al., "Cyclin D1 Overexpression in Mouse Epidermis Increases Cyclin-dependent Kinase Activity and Cell Proliferation in Vivo but Does Not Affect Skin Tumor Development", Cell Growth & Differentiation, Jul. 1999, vol. 10, pp. 467-472.

Rodriguez-Puebla et al., "cdk4 Deficiency Inhibits Skin Tumor Development but Does Not Affect Normal Keratinocyte Proliferation", American Journal of Pathology, August 2002, vol. 161, No. 2, pp. 405-411.

Shan et al., "Deregulated Expression of E2F-1 Induces S-Phase Entry and Leads to Apoptosis", Molecular and Cellular Biology, Dec. 1994, vol. 14, No. 12, pp. 8166-8173.

Sjoblom et al., "The Consensus Coding Sequences of Human Breast and Colorectal Cancers", Science, Oct. 13, 2006, vol. 314, pp. 268-274.

Tewari et al., "Yama/CPP32B, a Mammalian Homolog of CED-3, Is a CrmA-Inhibitable Protease That Cleaves the Death Substrate Poly(ADP-Ribose) Polymerase", Cell, Jun. 2, 1995, vol. 81, pp. 801-809.

Warenius, Hilmar M., "Are critical normal gene products in cancer cells the real therapeutic targets?", Anticancer Res., Sep.-Oct. 2002, 5:2651-5. (Abstract Only).

* cited by examiner

Hilra-025 = cyc-[Pro-Arg-Gly-Pro-Arg-Pro-Val-Tryp-Tryp-Arg-Arg-Trp-Trp-Arg-Arg]

HILRA-Glu-01

HILRa-CL-17-ABC

Bright Field

DAPI

SEQUENCE LISTING

```
<160> NUMBER OF SEQ ID NOS: 23

<210> SEQ ID NO 1
<211> LENGTH: 6
<212> TYPE: PRT
<213> ORGANISM: Artificial Sequence
<220> FEATURE:
<223> OTHER INFORMATION: CDK4 fragment

<400> SEQUENCE: 1

Pro Arg Gly Pro Arg Pro
1               5

<210> SEQ ID NO 2
<211> LENGTH: 17
<212> TYPE: PRT
<213> ORGANISM: Artificial Sequence
<220> FEATURE:
<223> OTHER INFORMATION: HILR-001 Synthesized

<400> SEQUENCE: 2

Pro Arg Gly Pro Arg Pro Val Ala Leu Lys Leu Ala Leu Lys Leu Ala
1               5                   10                  15

Leu

<210> SEQ ID NO 3
<211> LENGTH: 17
<212> TYPE: PRT
<213> ORGANISM: Artificial Sequence
<220> FEATURE:
<223> OTHER INFORMATION: HILR-PRO-25 Synthesized

<400> SEQUENCE: 3

Pro Arg Gly Pro Arg Pro Val Trp Trp Arg Arg Trp Trp Arg Arg Trp
1               5                   10                  15

Trp

<210> SEQ ID NO 4
<211> LENGTH: 6
<212> TYPE: PRT
<213> ORGANISM: Artificial Sequence
<220> FEATURE:
<223> OTHER INFORMATION: Active region of peptide
<220> FEATURE:
<221> NAME/KEY: Dac
<222> LOCATION: (1)..(1)
<223> OTHER INFORMATION: Dac = amino acid residue of (7-methoxy-
     coumarin-4-yl)-Ala-OH
<220> FEATURE:
<221> NAME/KEY: Sar
<222> LOCATION: (3)..(3)
<223> OTHER INFORMATION: Sar = Sarcosine
<220> FEATURE:
<221> NAME/KEY: dmPro
<222> LOCATION: (4)..(4)
<223> OTHER INFORMATION: dmPro = 5, 5-dimethylproline
<220> FEATURE:
<221> NAME/KEY: Nap
<222> LOCATION: (6)..(6)
<223> OTHER INFORMATION: Nap = amino acid residue of 3-amino-3-(2-
     naphthyl)propionic acid

<400> SEQUENCE: 4

Xaa Arg Xaa Xaa Arg Xaa
1               5

<210> SEQ ID NO 5
<211> LENGTH: 6
```

```
<212> TYPE: PRT
<213> ORGANISM: Artificial Sequence
<220> FEATURE:
<223> OTHER INFORMATION: Alternative active region of peptide
<220> FEATURE:
<221> NAME/KEY: Dac
<222> LOCATION: (1)..(1)
<223> OTHER INFORMATION: Dac = amino acid residue of (7-methoxy-
      coumarin-4-yl)-Ala-OH
<220> FEATURE:
<221> NAME/KEY: Sar
<222> LOCATION: (3)..(3)
<223> OTHER INFORMATION: Sar = Sarcosine
<220> FEATURE:
<221> NAME/KEY: Nap
<222> LOCATION: (4)..(4)
<223> OTHER INFORMATION: Nap = amino acid residue of 3-amino-3-(2-
      naphthyl)propionic acid
<220> FEATURE:
<221> NAME/KEY: Nap
<222> LOCATION: (6)..(6)
<223> OTHER INFORMATION: Nap = amino acid residue of 3-amino-3-(2-
      naphthyl)propionic acid

<400> SEQUENCE: 5

Xaa Arg Xaa Xaa Arg Xaa
1               5

<210> SEQ ID NO 6
<211> LENGTH: 8
<212> TYPE: PRT
<213> ORGANISM: Artificial Sequence
<220> FEATURE:
<223> OTHER INFORMATION: SEQ ID NO:6 Synthesized
<220> FEATURE:
<221> NAME/KEY: Dac
<222> LOCATION: (2)..(2)
<223> OTHER INFORMATION: Dac = amino acid residue of (7-methoxy-
      coumarin-4-yl)-Ala-OH
<220> FEATURE:
<221> NAME/KEY: Sar
<222> LOCATION: (4)..(4)
<223> OTHER INFORMATION: Sar = Sarcosine
<220> FEATURE:
<221> NAME/KEY: dmPro
<222> LOCATION: (5)..(5)
<223> OTHER INFORMATION: dmPro = 5, 5-dimethylproline dmPro can be
      either (S) or (R) stereoisomer
<220> FEATURE:
<221> NAME/KEY: Nap
<222> LOCATION: (7)..(7)
<223> OTHER INFORMATION: Nap = amino acid residue of 3-amino-3-(2-
      naphthyl)propionic acid Nap can be either (S) or (R) stereoisomer

<400> SEQUENCE: 6

Cys Xaa Arg Xaa Xaa Arg Xaa Cys
1               5

<210> SEQ ID NO 7
<211> LENGTH: 8
<212> TYPE: PRT
<213> ORGANISM: Artificial Sequence
<220> FEATURE:
<223> OTHER INFORMATION: SEQ ID NO:7 Synthesized
<220> FEATURE:
<221> NAME/KEY: Dac
<222> LOCATION: (2)..(2)
<223> OTHER INFORMATION: Dac = amino acid residue of (7-methoxy-
      coumarin-4-yl)-Ala-OH
<220> FEATURE:
<221> NAME/KEY: Sar
<222> LOCATION: (4)..(4)
<223> OTHER INFORMATION: Sar = Sarcosine
<220> FEATURE:
<221> NAME/KEY: Nap
```

```
<222> LOCATION: (5)..(5)
<223> OTHER INFORMATION: Nap = amino acid residue of 3-amino-3-(2-
      naphthyl)propionic acid Nap can be (S) or (R) stereoisomer
<220> FEATURE:
<221> NAME/KEY: Nap
<222> LOCATION: (7)..(7)
<223> OTHER INFORMATION: Nap = amino acid residue of 3-amino-3-(2-
      naphthyl)propionic acid Nap can be (S) or (R) stereoisomer

<400> SEQUENCE: 7

Cys Xaa Arg Xaa Xaa Arg Xaa Cys
1               5

<210> SEQ ID NO 8
<211> LENGTH: 8
<212> TYPE: PRT
<213> ORGANISM: Artificial Sequence
<220> FEATURE:
<223> OTHER INFORMATION: HILRa-CL-01 Synthesized

<400> SEQUENCE: 8

Cys Pro Arg Gly Pro Arg Pro Cys
1               5

<210> SEQ ID NO 9
<211> LENGTH: 10
<212> TYPE: PRT
<213> ORGANISM: Artificial Sequence
<220> FEATURE:
<223> OTHER INFORMATION: HILRa-CL-02 Synthesized
<220> FEATURE:
<221> NAME/KEY: Sar
<222> LOCATION: (2)..(2)
<223> OTHER INFORMATION: X = Sarcosine
<220> FEATURE:
<221> NAME/KEY: Sar
<222> LOCATION: (9)..(9)
<223> OTHER INFORMATION: X = Sarcosine

<400> SEQUENCE: 9

Cys Xaa Pro Arg Gly Pro Arg Pro Xaa Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: HILRa-CL-03 Synthesized
<220> FEATURE:
<221> NAME/KEY: Sar
<222> LOCATION: (2)..(2)
<223> OTHER INFORMATION: X = Sarcosine
<220> FEATURE:
<221> NAME/KEY: Sar
<222> LOCATION: (3)..(3)
<223> OTHER INFORMATION: X = Sarcosine
<220> FEATURE:
<221> NAME/KEY: Sar
<222> LOCATION: (10)..(10)
<223> OTHER INFORMATION: X = Sarcosine
<220> FEATURE:
<221> NAME/KEY: Sar
<222> LOCATION: (11)..(11)
<223> OTHER INFORMATION: X = Sarcosine

<400> SEQUENCE: 10

Cys Xaa Xaa Pro Arg Gly Pro Arg Pro Xaa Xaa Cys
1               5                   10

<210> SEQ ID NO 11
```

-continued

```
<211> LENGTH: 8
<212> TYPE: PRT
<213> ORGANISM: Artificial Sequence
<220> FEATURE:
<223> OTHER INFORMATION: HILRa-CL-04

<400> SEQUENCE: 11

Cys Pro Lys Gly Pro Arg Pro Cys
1               5

<210> SEQ ID NO 12
<211> LENGTH: 10
<212> TYPE: PRT
<213> ORGANISM: Artificial Sequence
<220> FEATURE:
<223> OTHER INFORMATION: HILRa-CL-05 Synthesized
<220> FEATURE:
<221> NAME/KEY: Sar
<222> LOCATION: (2)..(2)
<223> OTHER INFORMATION: X = Sarcosine
<220> FEATURE:
<221> NAME/KEY: Sar
<222> LOCATION: (9)..(9)
<223> OTHER INFORMATION: X = Sarcosine

<400> SEQUENCE: 12

Cys Xaa Pro Lys Gly Pro Arg Pro Xaa Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: HILRa-CL-06 Synthesized
<220> FEATURE:
<221> NAME/KEY: Sar
<222> LOCATION: (2)..(2)
<223> OTHER INFORMATION: X = Sarcosine
<220> FEATURE:
<221> NAME/KEY: Sar
<222> LOCATION: (3)..(3)
<223> OTHER INFORMATION: X = Sarcosine
<220> FEATURE:
<221> NAME/KEY: Sar
<222> LOCATION: (10)..(10)
<223> OTHER INFORMATION: X = Sarcosine
<220> FEATURE:
<221> NAME/KEY: Sar
<222> LOCATION: (11)..(11)
<223> OTHER INFORMATION: X = Sarcosine

<400> SEQUENCE: 13

Cys Xaa Xaa Pro Lys Gly Pro Arg Pro Xaa Xaa Cys
1               5                   10

<210> SEQ ID NO 14
<211> LENGTH: 8
<212> TYPE: PRT
<213> ORGANISM: Artificial Sequence
<220> FEATURE:
<223> OTHER INFORMATION: HILRa-CL-07 Synthesized

<400> SEQUENCE: 14

Cys Pro Arg Gly Pro Lys Pro Cys
1               5

<210> SEQ ID NO 15
<211> LENGTH: 10
<212> TYPE: PRT
<213> ORGANISM: Artificial Sequence
```

-continued

```
<220> FEATURE:
<223> OTHER INFORMATION: HILRa-CL-08 Synthesized
<220> FEATURE:
<221> NAME/KEY: Sar
<222> LOCATION: (2)..(2)
<223> OTHER INFORMATION: X = Sarcosine
<220> FEATURE:
<221> NAME/KEY: Sar
<222> LOCATION: (9)..(9)
<223> OTHER INFORMATION: X = Sarcosine

<400> SEQUENCE: 15

Cys Xaa Pro Arg Gly Pro Lys Pro Xaa Cys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: HILRa-CL-9 Synthesized
<220> FEATURE:
<221> NAME/KEY: Sar
<222> LOCATION: (2)..(2)
<223> OTHER INFORMATION: X = Sarcosine
<220> FEATURE:
<221> NAME/KEY: Sar
<222> LOCATION: (3)..(3)
<223> OTHER INFORMATION: X = Sarcosine
<220> FEATURE:
<221> NAME/KEY: Sar
<222> LOCATION: (10)..(10)
<223> OTHER INFORMATION: X = Sarcosine
<220> FEATURE:
<221> NAME/KEY: Sar
<222> LOCATION: (11)..(11)
<223> OTHER INFORMATION: X = Sarcosine

<400> SEQUENCE: 16

Cys Xaa Xaa Pro Arg Gly Pro Lys Pro Xaa Xaa Cys
1               5                   10

<210> SEQ ID NO 17
<211> LENGTH: 8
<212> TYPE: PRT
<213> ORGANISM: Artificial Sequence
<220> FEATURE:
<223> OTHER INFORMATION: HILRa-CL-10 Synthesized

<400> SEQUENCE: 17

Cys Pro Lys Gly Pro Lys Pro Cys
1               5

<210> SEQ ID NO 18
<211> LENGTH: 10
<212> TYPE: PRT
<213> ORGANISM: Artificial Sequence
<220> FEATURE:
<223> OTHER INFORMATION: HILRa-CL-11 Synthesized
<220> FEATURE:
<221> NAME/KEY: Sar
<222> LOCATION: (2)..(2)
<223> OTHER INFORMATION: X = Sarcosine
<220> FEATURE:
<221> NAME/KEY: Sar
<222> LOCATION: (9)..(9)
<223> OTHER INFORMATION: X = Sarcosine

<400> SEQUENCE: 18

Cys Xaa Pro Lys Gly Pro Lys Pro Xaa Cys
1               5                   10
```

```
<210> SEQ ID NO 19
<211> LENGTH: 12
<212> TYPE: PRT
<213> ORGANISM: Artificial Sequence
<220> FEATURE:
<223> OTHER INFORMATION: HILRa-CL-12 Synthesized
<220> FEATURE:
<221> NAME/KEY: Sar
<222> LOCATION: (2)..(2)
<223> OTHER INFORMATION: X = Sarcosine
<220> FEATURE:
<221> NAME/KEY: Sar
<222> LOCATION: (3)..(3)
<223> OTHER INFORMATION: X = Sarcosine
<220> FEATURE:
<221> NAME/KEY: Sar
<222> LOCATION: (10)..(10)
<223> OTHER INFORMATION: X = Sarcosine
<220> FEATURE:
<221> NAME/KEY: Sar
<222> LOCATION: (11)..(11)
<223> OTHER INFORMATION: X = Sarcosine

<400> SEQUENCE: 19

Cys Xaa Xaa Pro Lys Gly Pro Lys Pro Xaa Xaa Cys
1               5                   10

<210> SEQ ID NO 20
<211> LENGTH: 8
<212> TYPE: PRT
<213> ORGANISM: Artificial Sequence
<220> FEATURE:
<223> OTHER INFORMATION: HILRa CL-14 Synthesized
<220> FEATURE:
<221> NAME/KEY: Dac
<222> LOCATION: (2)..(2)
<223> OTHER INFORMATION: Dac = amino acid residue of (7-methoxy-
      coumarin-4-yl)-Ala-OH
<220> FEATURE:
<221> NAME/KEY: Hca
<222> LOCATION: (3)..(3)
<223> OTHER INFORMATION: Hca = amino acid residue of homocysteic acid
<220> FEATURE:
<221> NAME/KEY: Sar
<222> LOCATION: (4)..(4)
<223> OTHER INFORMATION: Sar = Sarcosine
<220> FEATURE:
<221> NAME/KEY: Hca
<222> LOCATION: (6)..(6)
<223> OTHER INFORMATION: Hca = amino acid residue of homocysteic acid
<220> FEATURE:
<221> NAME/KEY: Nap
<222> LOCATION: (7)..(7)
<223> OTHER INFORMATION: Nap = amino acid residue of 3-amino-3-(2-
      naphthyl)propionic acid

<400> SEQUENCE: 20

Cys Xaa Xaa Xaa Pro Xaa Xaa Cys
1               5

<210> SEQ ID NO 21
<211> LENGTH: 8
<212> TYPE: PRT
<213> ORGANISM: Artificial Sequence
<220> FEATURE:
<223> OTHER INFORMATION: HILRa CL-16 Synthesized
<220> FEATURE:
<221> NAME/KEY: Dac
<222> LOCATION: (2)..(2)
<223> OTHER INFORMATION: Dac = amino acid residue of (7-methoxy-
      coumarin-4-yl)-Ala-OH
<220> FEATURE:
<221> NAME/KEY: Hca
<222> LOCATION: (3)..(3)
```

-continued

```
<223> OTHER INFORMATION: Hca = amino acid residue of homocysteic acid
<220> FEATURE:
<221> NAME/KEY: Sar
<222> LOCATION: (4)..(4)
<223> OTHER INFORMATION: Sar = Sarcosine
<220> FEATURE:
<221> NAME/KEY: Nap
<222> LOCATION: (5)..(5)
<223> OTHER INFORMATION: Nap = amino acid residue of 3-amino-3-(2-
      naphthyl)propionic acid
<220> FEATURE:
<221> NAME/KEY: Hca
<222> LOCATION: (6)..(6)
<223> OTHER INFORMATION: Hca = amino acid residue of homocysteic acid
<220> FEATURE:
<221> NAME/KEY: Nap
<222> LOCATION: (7)..(7)
<223> OTHER INFORMATION: Nap = amino acid residue of 3-amino-3-(2-
      naphthyl)propionic acid

<400> SEQUENCE: 21

Cys Xaa Xaa Xaa Xaa Xaa Xaa Cys
1               5

<210> SEQ ID NO 22
<211> LENGTH: 18
<212> TYPE: PRT
<213> ORGANISM: Artificial Sequence
<220> FEATURE:
<223> OTHER INFORMATION: DAC peptide Synthesised
<220> FEATURE:
<221> NAME/KEY: Dac
<222> LOCATION: (7)..(7)
<223> OTHER INFORMATION: Dac - amino acid residue of (7-methoxy-
      coumarin-4-yl)-Ala-OH
<220> FEATURE:
<221> NAME/KEY: misc_feature
<222> LOCATION: (8)..(8)
<223> OTHER INFORMATION: Xaa can be any naturally occurring amino acid

<400> SEQUENCE: 22

Cys Pro Arg Gly Pro Arg Pro Xaa Trp Trp Arg Arg Trp Trp Arg Arg
1               5                   10                  15

Trp Trp

<210> SEQ ID NO 23
<211> LENGTH: 15
<212> TYPE: PRT
<213> ORGANISM: Artificial Sequence
<220> FEATURE:
<223> OTHER INFORMATION: Hilra-025 Synthesized

<400> SEQUENCE: 23

Pro Arg Gly Pro Arg Pro Val Trp Trp Arg Arg Trp Trp Arg Arg
1               5                   10                  15
```

CYCLIC PEPTIDE USEFUL IN THE TREATMENT OF CANCER

CROSS REFERENCE TO RELATED APPLICATIONS

This application is a U.S. National Stage Application filed under 35 U.S.C. § 371, and claims priority to International Application No. PCT/GB2020/0050804, filed Mar. 25, 2020, which application claims priority to Great Britain Application No. 1904099.7, filed Mar. 25, 2019, the disclosure of which are incorporated herein by reference.

FIELD OF THE INVENTION

The present invention relates to cyclic peptides useful in the treatment of cancer. The present invention also relates to medical uses of such peptides.

BACKGROUND OF THE INVENTION

The main thrust in anticancer drug development at present derives from the explosion of knowledge of cell surface receptors and positive and negative signal transduction factors, recently further fuelled by genomic studies of several common human cancers. Such studies have revealed a multitude of genetic mutations, hundreds of which are believed to be driver mutations involving critical proteins on signal transduction pathways that contribute to the evolution of autonomous cancer cell proliferation.

A multiplicity of potential drug targets are being revealed by this approach, with an even greater number of potential therapeutic agents, as several different drugs may show activity against any one target.

The present anticancer therapeutic paradigm envisages progress towards tailored drug treatment for individually selected cancers on the basis of their genomic mutation patterns. The resulting therapeutics are being rapidly introduced into the clinic. These new drugs, however, have generally poor single agent efficacy, with very few complete tumour responses, and median response durations of less than a year in the majority of cases.

Thus, there is a need for more global anticancer therapeutic agents.

Cyclin-dependent kinase 4 (CDK4) is an enzyme involved in the regulation of the cell cycle. In particular, activated CDK4 results in the phosphorylation of retinoblastoma (Rb) protein which leads to G1/S cell cycle transition. In addition, CDK4 phosphorylates other proteins involved in cell cycle control. Due to the role of CDK4 in promoting cell division, a number of studies of the role of CDK4 in cancer have been undertaken and CDK4 inhibitors have been implicated as possible therapies for several cancer types.

WO 2005/123760 describes peptides which comprise an amino acid sequence which is part of the amino acid sequence of the CDK4 protein. These peptides, which may be linear or cyclic, inhibit the growth of cancer cells. However, the specific activity of these peptides is relatively low and thus, their application in therapy is somewhat limited.

Further peptides based on CDK4 were described in WO 2009/112536. The cyclic peptides described in this document are composed of an active PRGPRP (SEQ ID NO:1) site "warhead" and an amphiphilic "backbone" forming a 16-18 amino acid cyclic peptide. These peptides, for example HILR-001 (Pro-Arg-Gly-Pro-Arg-Pro-Val-Ala-Leu-Lys-Leu-Ala-Leu-Lys-Leu-Ala-Leu) (SEQ ID NO:2), were shown to have an $IC_{50}$ of 200 μM and showed selective killing of H460 human non-small cell lung cancer cell lines and not primary diploid human fibroblasts, keratinocytes or MRC5 cells, in vitro. However, although such peptides had anti-cancer effects, they were not candidates for in vivo cancer therapy due to extremely high concentrations being required to obtain a local effect.

Since the abovementioned peptides were not candidates for in vivo therapy, new "backbones" were designed in attempts to make cyclic amphiphilic peptides containing the PRGPRP "warhead" more effective, through increased cell membrane penetration. HILR-PRO-25 (Pro-Arg-Gly-Pro-Arg-Pro-Val-Trp-Trp-Arg-Arg-Trp-Trp-Arg-Arg-Trp-Trp) (SEQ ID NO:3) as described in WO 2016/020437, showed the greatest improvement in cancer cell killing in vitro without lethality in MRC-5 cells; the $IC_{50}$ for HILR-PRO-25 on the RT112 bladder cancer cell line was 10 μM. However, the specific activity of HILR-PRO-025 was not sufficiently high for further development as an in vivo therapeutic. In addition, some experiments indicated that the increase cancerocidal effect was, in part, due to a non-specific contribution to cell killing by the HILR-PRO-25 backbone.

It is an object of the present invention to obviate or mitigate one or more of the abovementioned problems.

It is a further object of the present invention to identify new and improved compounds which have selective cancer cell killing ability and/or which have improved specific activity.

SUMMARY OF INVENTION

The present invention relates to cyclic peptides useful in the treatment of cancer and is based, in part, on investigations by the inventor in which he has surprisingly found that particular 'warhead' peptides are able to selectively kill cancer cells with high activity.

According to a first aspect of the present invention, there is provided a cyclic peptide comprising an active region which comprises the amino acid sequence $X^1X^2X^3X^4X^5X^6$ or a salt, derivative, prodrug or mimetic thereof, wherein:

$X^2$ and $X^5$ are arginine; and wherein either:

$X^1$ is (7-methoxy-coumarin-4-yl)-Ala-OH (Dac) and $X^3$, $X^4$ and $X^6$ are any amino acid; or $X^3$ is sarcosine (Sar) and $X^1$, $X^4$ and $X^6$ are any amino acid; or $X^4$ is 5,5-dimethylproline (dmPro) or 3-amino-3-(2-naphthyl)propionic acid (Nap) and $X^1$, $X^3$ and $X^6$ are any amino acid; or $X^6$ is Nap and $X^1$, $X^3$ and $X^4$ are any amino acid.

The inventor has surprisingly found that by providing a peptide according to the present invention, selective killing of cancer cells can be achieved. Such selectivity allows far lower drug concentrations to be used in the treatment of cancer and prevents unwanted side-effects often associated with traditional chemotherapy.

The peptides of the present invention are analogues of a part of the amino acid sequence of CDK4, in particular analogues of Pro-Arg-Gly-Pro-Arg-Pro (SEQ ID NO:1).

Although amino acid sequences such as Pro-Arg-Gly-Pro-Arg-Pro (SEQ ID NO:1) have previously been described as useful anti-cancer agents, the peptides of the present invention have been surprisingly found to be significantly more effective.

Contemplated herein are compounds which are salts, derivatives, prodrugs or mimetics of the cyclic peptides.

When the cyclic peptides comprise an ionisable functional group, the peptide may be provided in the form of a salt with an appropriate counterion. The counterion is preferably a pharmaceutically-acceptable counterion. The skilled person will be familiar with the preparation of salts.

If the peptide comprises acidic functional groups, the counterion may be an alkali metal or alkaline earth metal ion, for example. A preferred counterion for acidic compounds is sodium.

If the cyclic peptide comprises basic amino acid residues, a salt may be formed with a strong acid or a weak acid. For example, the compound could be provided as a hydrochloride salt, a hydrogen citrate salt, a hydrogen tosylate salt, or the like.

Derivatives of the peptides described herein are also contemplated. A derivative is a compound having substantially similar structure and function to the peptides defined herein, but which deviates slightly from the defined structures, for example by including one or more protecting groups and/or up to two additions, omissions, or substitutions of amino acid residues.

As used herein, the term "derivative" encompasses peptides in which the amino acid side-chains present in the compound are provided as protected amino acid side chains. The skilled person will be familiar with the use of protecting groups.

Derivatives further encompass compounds having greater than 85%, 90%, 92%, 95% or 99% sequence homology to the peptides defined herein. To form a derivative of a peptide defined herein, one amino acid residue may be omitted, replaced or inserted. Two amino acid residues may be omitted, replaced or inserted.

Also contemplated herein are pro-drugs of the cyclic peptide. A pro-drug is a peptide which is metabolised in vivo to produce the cyclic peptide. The skilled person will be familiar with the preparation of pro-drugs.

Also contemplated herein are peptide mimetics. A peptide mimetic is an organic compound having similar geometry and polarity to the peptides defined herein, and which has a substantially similar function. A mimetic may be a compound in which the NH groups of one or more peptide links are replaced by $CH_2$ groups. A mimetic may be a compound in which one or more amino acid residues is replaced by an aryl group, such as a napthyl group. Generally, peptide mimetics may be thought of as derivatives of peptides in which one or more of the amino acid residues is replaced by an optionally-substituted napthyl group, an optionally-substituted 1,2-dihydronapthyl group, an optionally-substituted 1,2,3,4-tetrahydronapthyl group bearing a substituent, or an optionally-substituted propyl group, for example. Substituents, if present, are typically selected from those groups which form the side-chains of any of the 23 proteinogenic amino acids.

The term "any amino acid" as used throughout the specification is not limited to only naturally occurring amino acids but also includes non-standard unnatural amino acid residues, for example. As such, some of the appended sequences and sequences described throughout the specification comprise non-standard unnatural amino acid residues. Throughout the present disclosure, the abbreviation. "Sar" refers to the amino acid residue of sarcosine. "Dac" refers to the amino acid residue of (7-methoxy-coumarin-4-yl)-Ala-OH. "Dm-Pro" refers to the amino acid residue of 5,5-dimethylproline. "Nap" refers to the amino acid residue of 3-amino-3-(2-naphthyl)propionic acid. "Hca" refers to the amino acid residue of homocysteic acid.

Through detailed investigations, the present inventor has surprisingly found that the charged residues in previous Pro-Arg-Gly-Pro-Arg-Pro (SEQ ID NO:1) peptides result in the peptide having a hydrophilicity which has been found to impair uptake of the peptide into cells. The present inventor has found that by introducing highly non-polar residues, the cytotoxic activity of the resultant peptides is improved.

Therefore, in embodiments of the present invention, there is provided a cyclic peptide comprising an active region which comprises the amino acid sequence $X^1X^2X^3X^4X^5X^6$ or a salt, derivative, prodrug or mimetic thereof, wherein:

$X^2$ and $X^5$ are arginine; and wherein either:

$X^1$ is Dac and $X^3$, $X^4$ and $X^6$ are any non-polar amino acid; or $X^3$ is Sar and $X^1$, $X^4$ and $X^6$ are any non-polar amino acid; or $X^4$ is dmPro or Nap and $X^1$, $X^3$ and $X^6$ are any non-polar amino acid; or $X^6$ is Nap and $X^1$, $X^3$ and $X^4$ are any non-polar amino acid.

The non-polar amino acids may include non-naturally occurring amino acids such as, for example, Dac, Sar, Nap and/or DmPro. The present inventor has found that the use of such non-naturally occurring amino acids provides resistance to peptidolysis and thus, results in improved cytotoxic activity.

In embodiments in which $X^1$ is Dac, $X^3$ may be Sar and/or $X^4$ may be dmPro or Nap and/or $X^6$ may be Nap.

In embodiments in which $X^3$ is Sar, $X^1$ may be Dac and/or $X^4$ may be dmPro or Nap and/or $X^6$ may be Nap.

In embodiments in which $X^4$ is dmPro or Nap, $X^1$ may be Dac and/or $X^3$ may be Sar and/or $X^6$ may be Nap.

In embodiments in which $X^6$ is Nap, $X^1$ may be Dac and/or $X^3$ may be Sar and/or $X^4$ may be dmPro or Nap.

In embodiments of the present application, $X^4$ is dmPro or Nap. The present inventor has found that the presence of one of these residues at the $X^4$ position results in an improved cancer cell toxicity. Surprisingly, when $X^4$ is Nap, the cancer cell toxicity of the resultant peptide is around 4-5× greater than when $X^4$ is dmPro. Therefore, in preferred embodiments of the invention $X^4$ is Nap.

The present inventor has surprisingly found that the length of the active region of the peptide has an effect on the cytotoxic activity of the peptides. Without being bound by theory, it is believed that conformational constraint of the peptides is likely to play a part in their activity.

In a preferred embodiment of the invention, the active region of the peptide is between 4 and 10 amino acids in length, more preferably between 6 and 10 amino acids in length. In embodiments of the invention, the active region of the peptide may be 6, 8 or 10 amino acids in length. In embodiments, the active region of the peptide may be 6 amino acids in length. The present inventor has surprisingly shown that a peptide length of 6 amino acids results in a higher level of cancer cell cytotoxicity.

In embodiments of the invention, the active region of the peptide comprises the amino acid sequence:

(SEQ ID NO: 4)
Dac-Arg-Sar-dmPro-Arg-Nap.

5

In embodiments of the invention, the active region of the peptide consists of the amino acid sequence:

(SEQ ID NO: 4)
Dac-Arg-Sar-dmPro-Arg-Nap i.e. the active region of the peptide is 6 amino acids in length.

In alternative embodiments of the invention, the active region of the peptide comprises the amino acid sequence:

(SEQ ID NO: 5)
Dac-Arg-Sar-Nap-Arg-Nap.

In embodiments of the invention, the active region of the peptide consists of the amino acid sequence:

(SEQ ID NO: 5)
Dac-Arg-Sar-Nap-Arg-Nap i.e. the active region of the peptide is 6 amino acids in length.

The peptides of the present invention are cyclic. The skilled person will appreciate that there are numerous ways in which the peptides of the present invention could be cyclised. For example, an amide bond could be formed between a carboxylic acid group and an amine group on the N- and C-termini of the peptide, respectively. The skilled person will appreciate how formation of an amide bond could be achieved, for example, by reaction of the carboxylic acid with a coupling agent (for example a carbodiimide or an aminium/uranium coupling agent).

Alternatively, another type of bond or linkage could be formed between the residues at the N- or C-termini of the peptide, or indeed between any side chains in the peptide. For example, in embodiments, the active region of the peptide may be flanked by cysteine residues i.e. one or more cysteine residues may be attached to the C- and N-terminal ends of the active region of the peptide.

In such embodiments, the peptide may be cyclised by one or more thioester bonds between the flanking cysteine residues. The skilled person will appreciate that the peptide may be cyclised by formation of one or more thioester bonds between any thiol group in the peptide chain, and not necessarily between the thiol groups of flanking cysteine residues.

In embodiments, the peptide may be cyclised by reacting two thiol groups in the peptide chain with a suitable linker, for example a di-benzyl bromide.

In a preferred embodiment of the invention, the active region of the peptide is flanked by cysteine residues. For example, in embodiments of the first aspect of the invention, the peptide may comprise the amino acid sequence: $Y^1A^1X^1X^2X^3X^4X^5X^6A^2Y^2$ or a salt, derivative, prodrug or mimetic thereof, wherein:

$A^1$ and $A^2$ may be present or absent, when $A^1$ and $A^2$ are present they comprise one or more amino acids; and $Y^1$ and $Y^2$ are cysteine.

$X^1, X^2, X^3, X^4, X^5, X^6$ are as described above. Preferably, when $A^1$ and $A^2$ are present they comprise non-polar amino acids. The non-polar amino acids may be one or more non-naturally occurring amino acid such as, for example, Dac, Sar, Nap and/or DmPro.

In preferred embodiments of the invention, the peptide may comprise the amino acid sequence:

(SEQ ID NO: 6)
Cys-Dac-Arg-Sar-dmPro-Arg-Nap-Cys.

In embodiments of the invention, the peptide may consist of the amino acid sequence:

(SEQ ID NO: 6)
Cys-Dac-Arg-Sar-dmPro-Arg-Nap-Cys.

In alternative preferred embodiments of the invention, the peptide may comprise the amino acid sequence:

(SEQ ID NO: 7)
Cys-Dac-Arg-Sar-Nap-Arg-Nap-Cys.

In embodiments of the invention, the peptide may consist of the amino acid sequence:

(SEQ ID NO: 7)
Cys-Dac-Arg-Sar-Nap-Arg-Nap-Cys.

In embodiments where the peptide comprises or consists of the amino acid sequence SEQ ID NO:6 or SEQ ID NO:7, it is preferred if the peptide is cyclised by reacting two thiol groups in the N- and C-terminal cysteine residues with a suitable linker, for example a di-benzyl bromide.

In embodiments of the present invention the peptide may be glycosylated. Cancer cells have altered glucose metabolism, frequently resulting in increased glucose uptake. The increased update of $_{18}F$ labelled fluorodeoxyglucose in PET clinical scanning for cancer is well established. Without wishing to be bound by theory, it is therefore expected that such glycosylation increases the uptake of the peptide of the invention into cancer cells.

The skilled person will appreciate how the peptide of the invention could be glycosylated. In embodiments, the peptide could be glycosylated with 2-deoxyglucose. For example, the peptide could glycosylated at hydroxyl groups present in the peptide of the present invention.

The peptides of the present invention may comprise amino acids of any suitable stereochemistry, as will be understood by the skilled person. In embodiments of the invention in which the peptide comprises or consists of the amino acid sequence Dac-Arg-Sar-dmPro-Arg-Nap (SEQ ID NO:4), Dac-Arg-Sar-Nap-Arg-Nap (SEQ ID NO:5), Cys-Dac-Arg-Sar-dmPro-Arg-Nap-Cys (SEQ ID NO:6) or Cys-Dac-Arg-Sar-Nap-Arg-Nap-Cys (SEQ ID NO:7) the peptides preferably comprise amino acids of the following stereochemistry:

SEQ ID NO: 4
(S)Dac-(S)Arg-Sar-(S)dmPro-(S)Arg-(S)Nap;
or
(S)Dac-(S)Arg-Sar-(S)dmPro-(S)Arg-(R)Nap;
or
(S)Dac-(S)Arg-Sar-(R))dmPro-(S)Arg-(S)Nap;
or
(S)Dac-(S)Arg-Sar-(R))dmPro-(S)Arg-(R))Nap

-continued

```
                                     SEQ ID NO: 5
(S)Dac-(S)Arg-Sar-(S)Nap-(S)Arg-(S)Nap;
or (S)Dac-(S)Arg-Sar-(S)Nap-(S)Arg-(R)Nap;
or (S)Dac-(S)Arg-Sar-(R)Nap-(S)Arg-(S)Nap;
or (S)Dac-(S)Arg-Sar-(R)Nap-(S)Arg-(R)Nap

SEQ ID NO: 6
(R)Cys-(S)Dac-(S)Arg-Sar-(S)dmPro-(S)Arg-(S)Nap- (R)Cys;
or (R)Cys-(S)Dac-(S)Arg-Sar-(S)dmPro-(S)Arg-(R)Nap- (R)Cys;
or (R)Cys-(S)Dac-(S)Arg-Sar-(R)dmPro-(S)Arg-(S)Nap- (R)Cys;
or (R)Cys-(S)Dac-(S)Arg-Sar-(R)dmPro-(S)Arg-(R)Nap- (R)Cys

SEQ ID NO: 7
(R)Cys-(S)Dac-(S)Arg-Sar-(S)Nap-(S)Arg-(S)Nap- (R)Cys;
or (R)Cys-(S)Dac-(S)Arg-Sar-(S)Nap-(S)Arg-(R)Nap- (R)Cys;
or (R)Cys-(S)Dac-(S)Arg-Sar-(R)Nap-(S)Arg-(S)Nap- (R)Cys;
or (R)Cys-(S)Dac-(S)Arg-Sar-(R)Nap-(S)Arg-(R)Nap- (R)Cys
```

In embodiments of the present invention, the peptide preferably comprises or consists of the amino acid sequence (S)Dac-(S)Arg-Sar-(S)dmPro-(S)Arg-(S)Nap. In embodiments of the present invention, the peptide preferably comprises or consists of the amino acid sequence (S)Dac-(S)Arg-Sar-(S)dmPro-(S)Arg-(R)Nap. In embodiments of the present invention, the peptide preferably comprises or consists of the amino acid sequence (S)Dac-(S)Arg-Sar-(R))dmPro-(S)Arg-(S)Nap. In embodiments of the present invention, the peptide preferably comprises or consists of the amino acid sequence (S)Dac-(S)Arg-Sar-(R))dmPro-(S)Arg-(R))Nap In embodiments of the present invention, the peptide preferably comprises or consists of the amino acid sequence (S)Dac-(S)Arg-Sar-(S)Nap-(S)Arg-(S)Nap. In embodiments of the present invention, the peptide preferably comprises or consists of the amino acid sequence (S)Dac-(S)Arg-Sar-(S)Nap-(S)Arg-(R)Nap. In embodiments of the present invention, the peptide preferably comprises or consists of the amino acid sequence (S)Dac-(S)Arg-Sar-(R)Nap-(S)Arg-(S)Nap. In embodiments of the present invention, the peptide preferably comprises or consists of the amino acid sequence (S)Dac-(S)Arg-Sar-(R)Nap-(S)Arg-(R)Nap.

In embodiments of the present invention, the peptide preferably comprises or consists of the amino acid sequence (R)Cys-(S)Dac-(S)Arg-Sar-(S)dmPro-(S)Arg-(S)Nap-(R) Cys. In embodiments of the present invention, the peptide preferably comprises or consists of the amino acid sequence (R)Cys-(S)Dac-(S)Arg-Sar-(S)dmPro-(S)Arg-(R)Nap-(R) Cys. In embodiments of the present invention, the peptide preferably comprises or consists of the amino acid sequence (R)Cys-(S)Dac-(S)Arg-Sar-(R)dmPro-(S)Arg-(S)Nap-(R) Cys. In embodiments of the present invention, the peptide preferably comprises or consists of the amino acid sequence (R)Cys-(S)Dac-(S)Arg-Sar-(R)dmPro-(S)Arg-(R)Nap-(R) Cys.

In embodiments of the present invention, the peptide preferably comprises or consists of the amino acid sequence (R)Cys-(S)Dac-(S)Arg-Sar-(S)Nap-(S)Arg-(S)Nap-(R)Cys. In embodiments of the present invention, the peptide preferably comprises or consists of the amino acid sequence (R)Cys-(S)Dac-(S)Arg-Sar-(S)Nap-(S)Arg-(R)Nap-(R)Cys. In embodiments of the present invention, the peptide preferably comprises or consists of the amino acid sequence (R)Cys-(S)Dac-(S)Arg-Sar-(R)Nap-(S)Arg-(S)Nap-(R)Cys. In embodiments of the present invention, the peptide preferably comprises or consists of the amino acid sequence (R)Cys-(S)Dac-(S)Arg-Sar-(R)Nap-(S)Arg-(R)Nap-(R) Cys.

In embodiments, the peptide of the present invention is cytotoxic to, or inhibits the growth of, a cancer cell. In this context, a cancer cell is a cell taken from a primary tumour, a metastasis or other suspected site of cancer in a subject, or a cell line derived from a cancer. It is preferred that the peptide is more cytotoxic to, or inhibitive to the growth of a cancer cell than a non-cancerous and/or a control cell. As used herein, the term "non-cancerous cell" is used to mean a normal (e.g. healthy) cell i.e. cells which do not have a cancerous phenotype. Such cells may be cells from any tissue in a subject. A control cell includes a normal non-cancerous cell and may be derived from the corresponding normal tissue of a patient or from a primary cell culture.

In further aspects of the present invention there are provided medical uses of the peptides of the invention. For example, in a second aspect of the invention there is provided a pharmaceutical composition comprising a peptide according to the first aspect of the present invention and a pharmaceutical acceptable carrier, diluent or excipient.

The skilled person will be familiar with the formulation of pharmaceutical compositions. Any appropriate carrier, diluent or excipient may be used and various combinations of carriers, diluents and excipients may be used.

In embodiments, the composition may comprise a further therapeutic agent. For example, such further therapeutic agents may comprise anticancer hormones and/or chemotherapeutic drugs.

The composition may be formulated for any desired method of administration, for example for oral administration or parenteral administration.

The peptides of the present invention are particularly useful in medicine. There is therefore also provided the peptide of the first aspect of the invention or the pharmaceutical composition of the second aspect of the invention for use in medicine.

The peptide and pharmaceutical composition of the present invention is effective in treating cancers of various origins, including breast cancer, prostate cancer, colorectal cancer, bladder cancer, ovarian cancer, endometrial cancer, cervical cancer, head and neck cancer, stomach cancer, pancreatic cancer, oesophagus cancer, small cell lung cancer, non-small cell lung cancer, malignant melanomas, neuroblastomas, leukaemias, lymphomas, sarcomas and gliomas.

There is therefore also provided the peptide of the first aspect of the invention or the pharmaceutical composition of the second aspect of the invention for use in the treatment of cancer.

It is expected that the peptides of the present invention will be useful in the treatment of a wide range of cancers. The cancer may be of various origins, but may include one or more of breast cancer, prostate cancer, colorectal cancer, bladder cancer, ovarian cancer, endometrial cancer, cervical cancer, head and neck cancer, stomach cancer, pancreatic cancer, oesophagus cancer, small cell lung cancer, non-small cell lung cancer, malignant melanomas, neuroblastomas, leukaemias, lymphomas, sarcomas and gliomas. Further, the peptides may be useful for the treatment of a patient suffering from multiple cancer types or metastatic cancer, for example.

The peptide or pharmaceutical composition may be administered with a further therapeutic agent, for example anticancer hormones, chemotherapeutic drugs and/or ionising radiation. In embodiments the peptide or pharmaceutical composition may be administered as part of a treatment regime with one or more conventional therapies such as chemotherapy, radiation therapy or surgery.

There is also provided the use of a peptide according to the first aspect of the invention in the manufacture of a medicament for the treatment of cancer.

The present invention further provides a method of treating cancer, the method comprising administering to a patient the peptide of the first aspect of the invention or the pharmaceutical composition of the second aspect of the invention.

The method may further comprise the use of one or more conventional therapies such as chemotherapy, radiation therapy or surgery.

In embodiments, the cancer comprises one or more of breast cancer, prostate cancer, colorectal cancer, bladder cancer, ovarian cancer, endometrial cancer, cervical cancer, head and neck cancer, stomach cancer, pancreatic cancer, oesophagus cancer, small cell lung cancer, non-small cell lung cancer, melanoma, neuroblastoma, leukaemia, lymphoma, sarcoma or glioma.

The described and illustrated embodiments are to be considered as illustrative and not restrictive in character, it being understood that only the preferred embodiments have been shown and described and that all changes and modifications that come within the scope of the inventions as defined in the claims are desired to be protected.

The optional features set out herein may be used either individually or in combination with each other where appropriate and particularly in the combinations as set out in the accompanying claims. The optional features for each aspect or exemplary embodiment of the invention as set out herein are also to be read as applicable to any other aspect or exemplary embodiments of the invention, where appropriate. In other words, the skilled person reading this specification should consider the optional features for each exemplary embodiment of the invention as interchangeable and combinable between different exemplary embodiments.

It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," or "at least one," are used to preface a feature there is no intention to limit the claim to only one such feature unless specifically stated to the contrary in the claim.

DETAILED DESCRIPTION

Without being bound by theory, the following mechanism is suggested to explain the mode of action of the peptides of the present invention:

PRGPRP Function in Normal Cells

Cdk4 with its cyclin D partners initiates the molecular processes which begin cell division by phosphorylating the retinoblastoma protein (pRb) and associated pRb family members (Harbour et al. Cell (1999); 98: 859-869), leading to the release of E2F-1 and associated proteins involved in the induction of the relevant enzymes for DNA synthesis (Classon and Harlow; Nature Reviews Cancer (2002) 2: 910-917). In addition to promoting cellular proliferation, however, E2F can induce apoptosis (Nevins et al., Hum Mol Genet. (2001); 10:699-703).

It is proposed that in normal diploid cells the PRGPRP (SEQ ID NO:1) region of Cdk4 guards against apoptosis by E2F-1 when the kinase region of Cdk4 phosphorylates the Rb protein and related family members. Protection against apoptosis is achieved by PRGPRP (SEQ ID NO:1) binding to the DEVD region of PARP and thus impeding caspase-3 (and others) binding to that site so that PARP is not cleaved. Cleavage of PARP-1 by caspases is considered to be a hallmark of apoptosis. [Kaufmann S H, et al: Specific proteolytic cleavage of poly(ADP-ribose) polymerase: an early marker of chemotherapy-induced apoptosis. Cancer Res 1993, 53:3976-3985. Tewari M, et al. Yama/CPP32 beta, a mammalian homolog of CED-3, is a CrmA inhibitable protease that cleaves the death substrate poly(ADP-ribose) polymerase. Cell 1995, 81:801-809]. Thus by "applying a brake" to PARP-cleavage, the PRGPRP domain of Cdk4 mediates against excessive apoptosis.

In normal cells there is little to no DNA damage so there will be minimal Poly(ADP-ribosylation) and the PRGPRP-protected uncleaved PARP will not deplete NAD+ which will remain at high enough levels.

PRGPRP Function in Early Multistage Carcinogenesis

Several reports indicate that Cdk4, in contrast to Cdk2 or Cdk6, appears to be the sole cyclin-dependent kinase whose functioning presence is mandatory for successful tumourigenesis (Warenius et al., Molecular Cancer (2011); 10: 72-88).

In summary: Cdk4 gene knockout in mice completely abrogates chemically induced epidermal carcinogenesis (Rodriguez-Puebla et al. 2002; Am J Pathol (2002); 161: 405-411), without effect on normal skin keratinocyte proliferation, despite the continuing presence of Cdk2 and Cdk6. Additionally, ablation of CDK4 (Miliani de Marval et al.; Mol Cell Biol. (2004); 24: 7538-7547) but not of CDK2 (Macias et al. 2007; Cancer Res 2007, 67:9713-9720) inhibits myc-mediated oral tumorigenesis. Furthermore, overexpression of Cdk4 but not cyclin D1 promotes mouse skin carcinogenesis (Rodriguez-Puebla et al. 1999; Cell Growth Differ 1999, 10:467-472), whilst elevated Cdk2 activity, despite inducing keratinocyte proliferation, is not tumorogenic (Macias et al., 2008).

Multistage carcinogenesis occurs as the result of deregulation of both cell proliferation and cell survival (Evan and Vousden 2001; Nature (2001); 411: 342-348). Activating mutations occur in genes promoting cell division and inactivating mutations occur in tumour suppressor genes. However, mutations that can activate the pathways leading to deregulation of E2F factors and promote increased cellular proliferation can also promote apoptosis (Quin et al. 1994; Proc. Natl Acad. Sci. USA (1994); 91: 10918-10922, Shan et al. 1994; Mol. Cell. Biol (1994); 14: 8166-8173). For carcinogenesis to progress successfully, cells must be able to maximise proliferation whilst avoiding apoptosis (Lowe and Lin 2000; Carcinogenesis (2000); 21: 485-495).

An explanation for the above findings could be that during carcinogenesis there is an increased likelihood of apoptosis as well as cellular proliferation. By binding to DEVD and preventing PARP cleavage, the PRGPRP motif inhibits apoptosis allowing tumours to form. In the absence of PRGPRP increased apoptosis will prevent tumour formation. Early in carcinogenesis DNA damage is minimal, cell division is not unrestrained and the cell is not operating under aerobic glycolysis, so preventing PARP cleavage will be unlikely to cause necrosis.

The observation that the presence of Cdk4 appears to be mandatory for successful carcinogenesis can therefore be explained, not by reference to the kinase activity of Cdk4, but rather by the activity of the externalised loop containing the PRGPRP motif, which binds to the DEVD region of PARP minimises apoptosis and allows increased cellular proliferation to progress.

In the absence of Cdk4 and its PRGPRP (SEQ ID NO: 1) site the carcinogenic process is likely to end in apoptosis rather than cell immortalisation.

The Effect of the PRGPRP Region of CDK4 in Fully Developed Cancer Cells

It has become increasingly apparent that the DNA in established cancer cells is vastly damaged (Warenius; Anticancer Res. (2002); 22:2651-2656). This high level of DNA damage is not a feature of early carcinogenesis but has been observed across a wide range of clinical cancers (Sjöblom et al., Science (2006): 314: 268-274; Greenman et al., 2007; Jones et al., Science (2008); 321: 1801-1806; Gerlinger et al., N Engl J Med (2012); 366: 883-892).

Significant DNA damage would be expected to stimulate PARP to carry out poly(ADP-ribosylation) at multiple sites, using up the available NAD+. Upregulation of PARP-1 has been described in many tumour types including breast, colon, endometrial, oesophagus, kidney, lung, ovary, skin, rectal stomach, thyroid and testisticular cancer (Ossovskaya et al. Genes and Cancer (2010); 1: 812-821). The cell also responds to DNA damage by activating the apoptotic pathway which involves caspase cleavage of PARP at the DEVD site thus inactivating poly(ADP-ribosylation) and allowing sufficient NAD+ to generate the ATP that is necessary for apoptosis. The survival of such advanced cancer cells is thus dependent on a balance between a tendency towards apoptotic death or necrotic death.

In addition the unrestrained division of cancer cells, in contrast to normal cells, requires increased energy for the synthesis of new cellular macromolecules and the accomplishment of mitosis.

Finally the Warburg effect in cancer cells makes them much more dependent on aerobic glycolysis (which may be increased as much as 200-fold) than on mitochondrial ATP generation.

By inhibiting PARP cleavage, the peptides of the present invention put stress on the cellular energy supplies. However, PARP agonists (and caspase inhibitors) do not cause the cancer cell necrosis seen with the present invention. For necrosis to occur a further stress is needed. Thus peptides of the present disclosure are likely to have an additional target to PARP such as lactate dehydrogenase (LDH), which is involved in the aerobic glycolysis characteristic of cancer cells.

In cancer cells the switch to aerobic glycolysis makes its energy systems very dependent on the supply of NAD produced by the activity of LDH. In this situation the cancer cell will be exquisitely sensitive to the competing demand of upregulated, active PARP for NAD to be used in poly-ADP-ribosylation. A compound whose action is like that described here for the cyclic peptides of the invention will be likely to be selectively toxic to cancer cells by agonising PARP and increasing its NAD utilisation at the same time as inhibiting LDH and lowering the availability of NAD, resulting in insufficient NAD for the glycolytic, Embden-Meyerhof pathway from glucose-6 phosphate to pyruvate.

Figure 2:
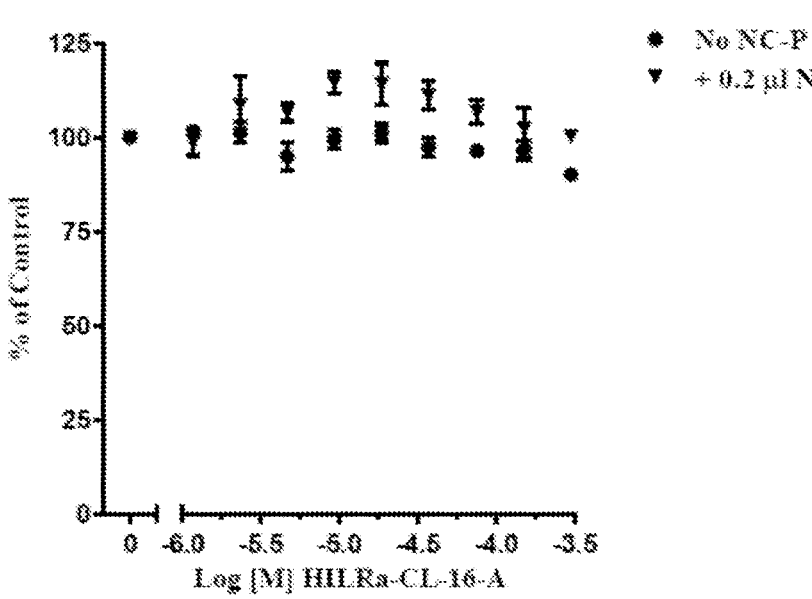
Figure 2:
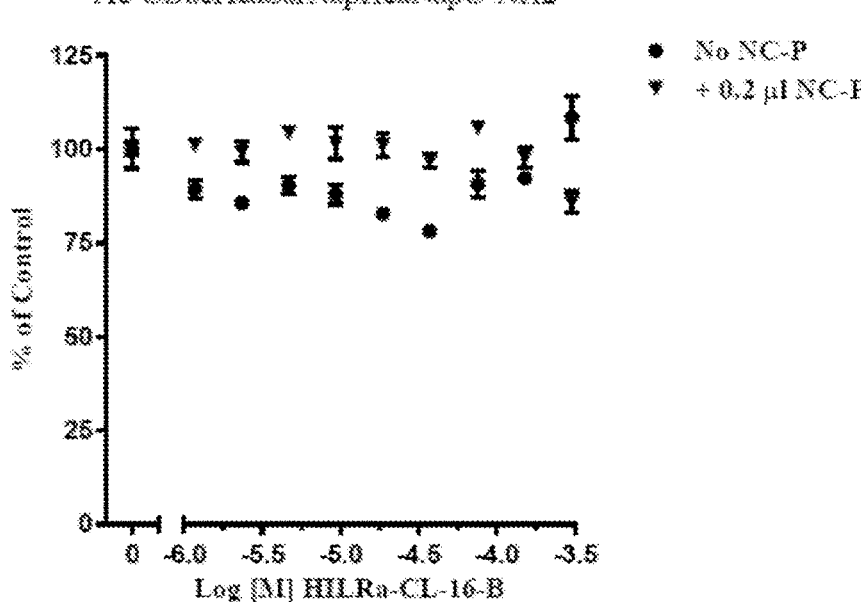
Figure 2:
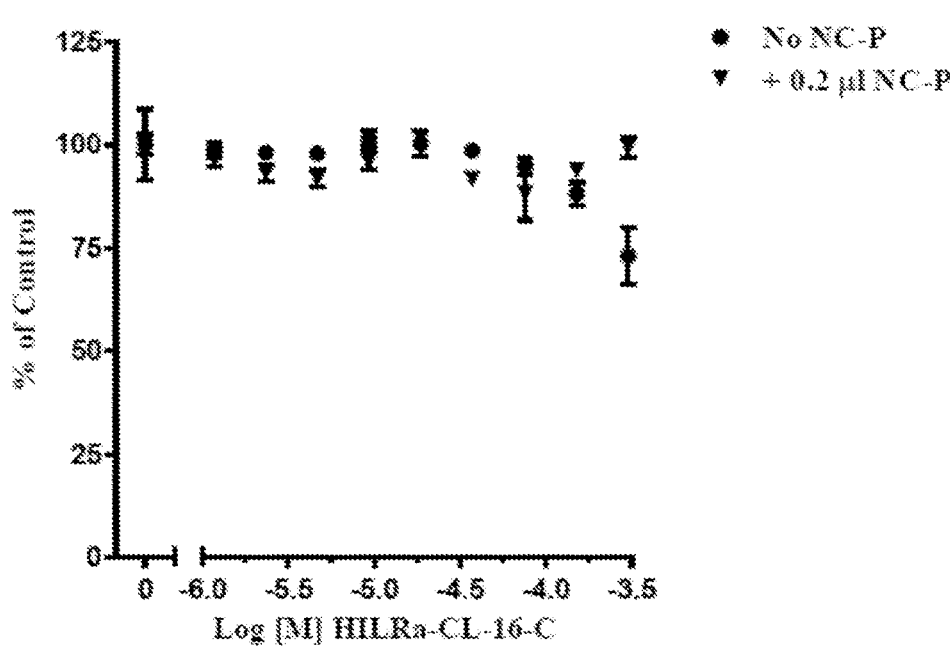
Figure 2:
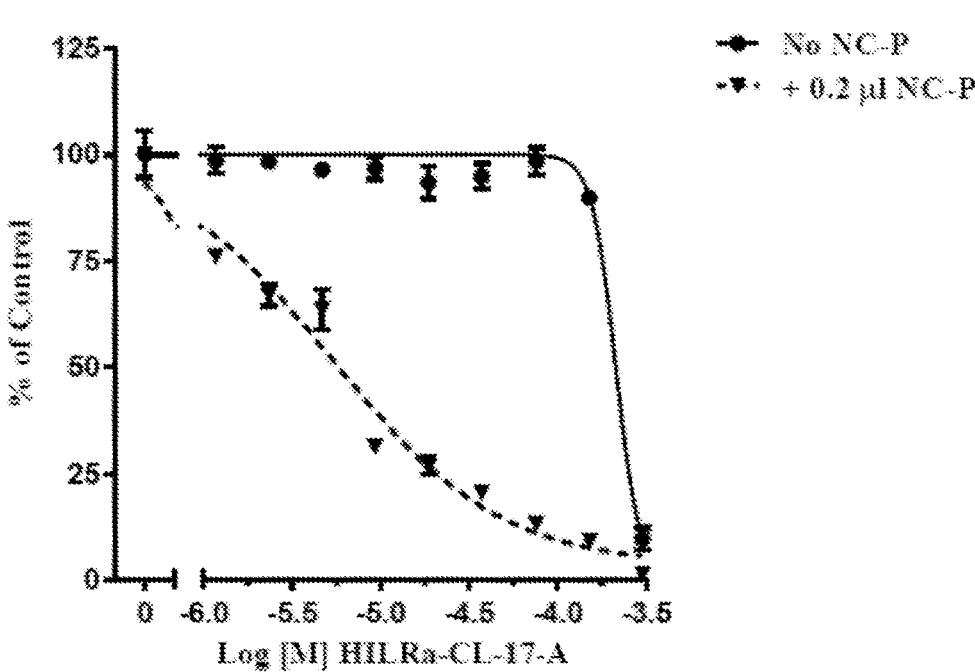
Figure 2:
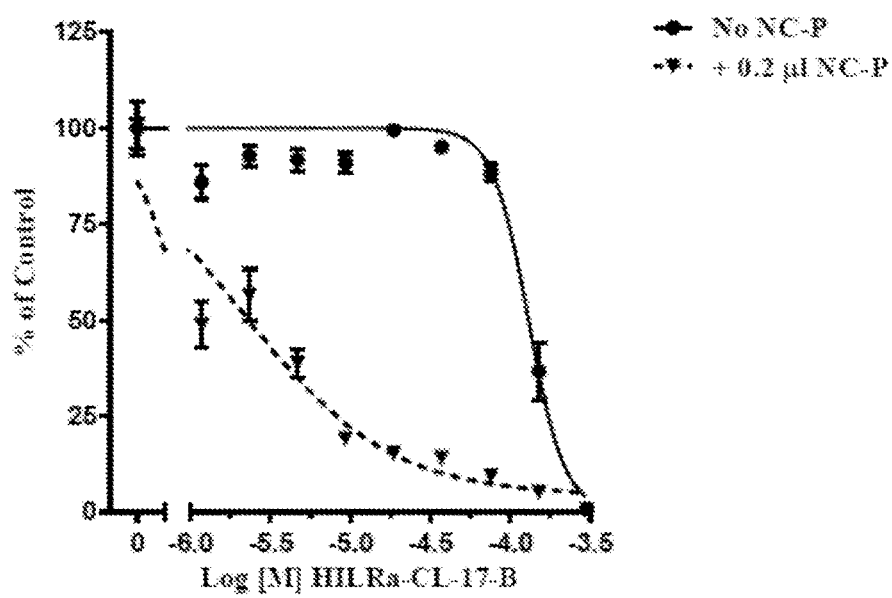
Figure 2:
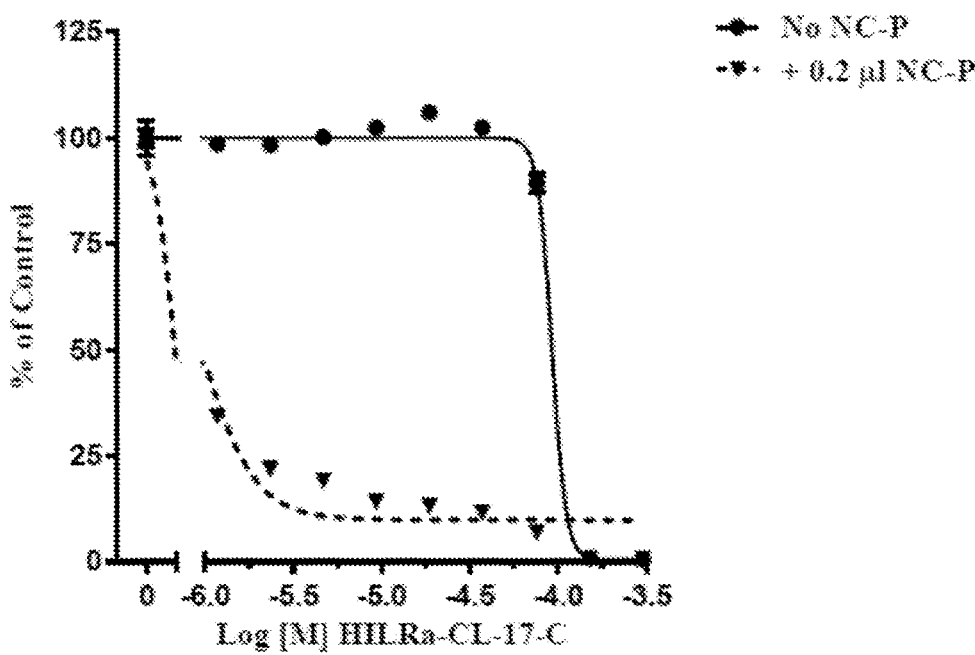
Figure 3:
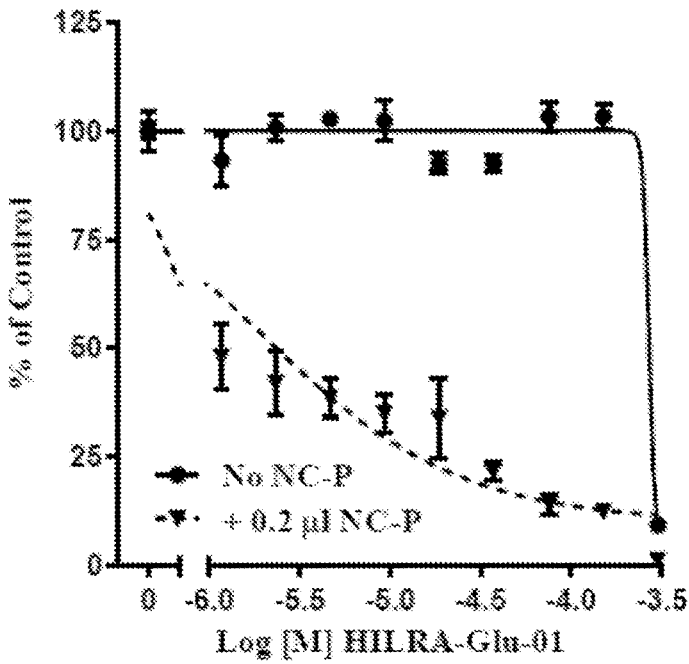
Figure 3:
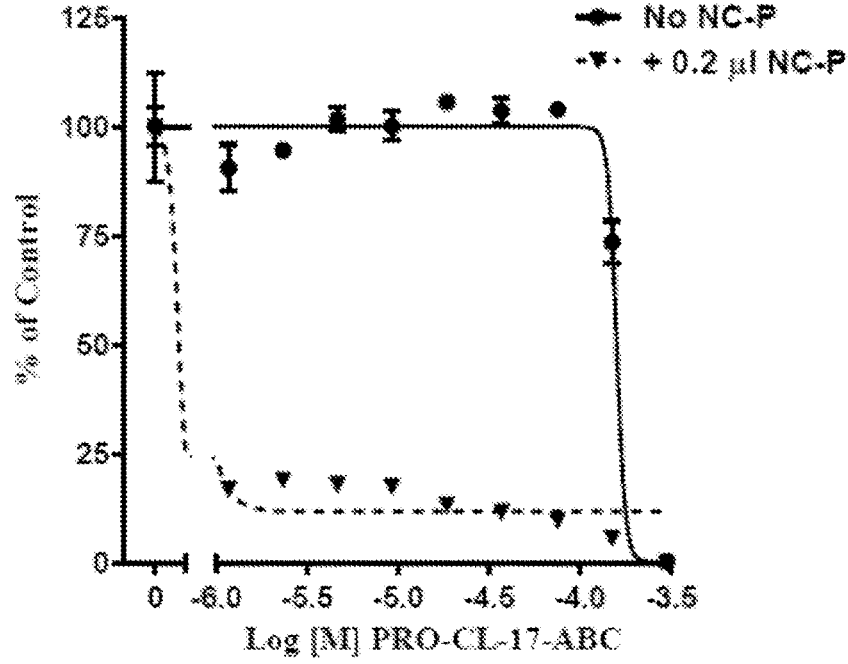

The present invention will now be further described with reference to the following figures which show:

FIG. 1: Human non-small cell lung cancer cell survival following treatment with Hilra-025, with and without Nanocin Pro™;

FIG. 2: H460 lung cancer cell survival curves following peptide exposure;

FIG. 3: NCI-H460 cell viability assays comparing the effect of a glycosylated peptide (HILRa-Glu-01) and an unglycosylated peptide (HILRa-CL-17); and FIG. 4: Distribution of DAC peptide Cys-[Pro-Arg-Gly-Pro-Arg-Pro-DAC-Trp-Trp-Arg-Arg-Trp-Tp-Arg-Arg-Trp-Trp] in the presence of Nanocin Pro™.

EXAMPLES

The present invention will now be described in further detail with reference to the following examples, which are provided for illustration only.

Figure 4:
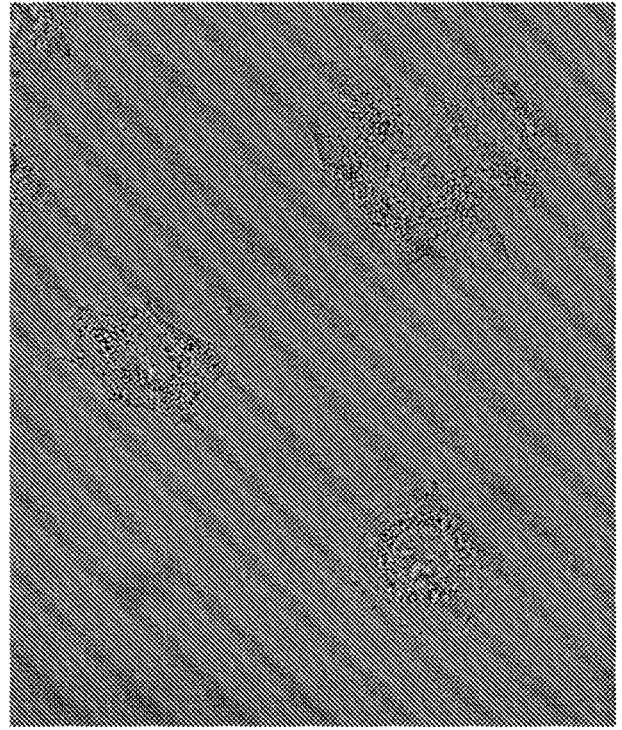
Figure 4:
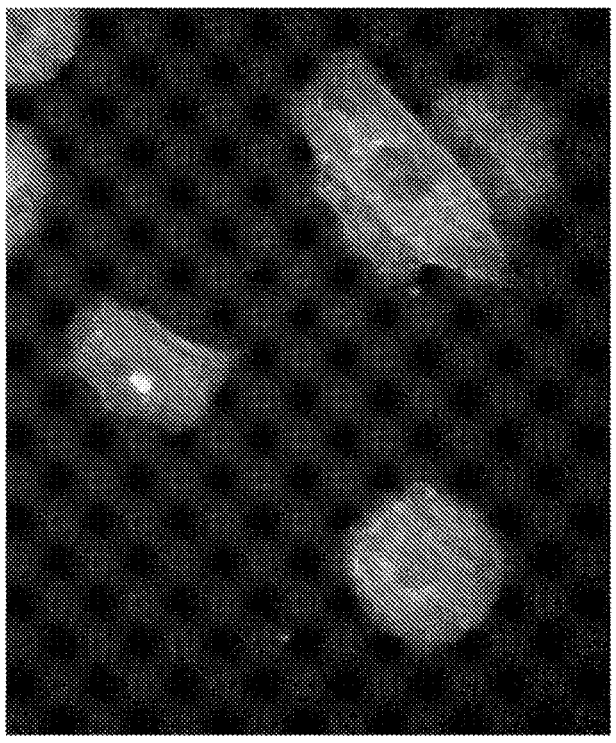

Example 1: Increased Internalisation Improves Potency of Cyclic Amphiphilic Peptides (FIGS. 1 and 4)

Poor uptake of drugs into cells is a common problem that blocks the drug development progress of many promising peptides and proteins. A nanoparticle reagent (Nanocin Pro™, Tecrea Limited) is available, which enables improved internalisation of biomolecules including peptides.

The present inventor tested the cytotoxicity of previously described cyclic peptides with and without Nanocin Pro™. Proliferation assays were performed to examine the effect of HilRa linear Peptide-025 on the viability NCI-H460 cells. Assays were performed in the presence and absence of the peptide transfection reagent Nanocin-PRO at concentrations of 0.1 µl, 0.2 µl and 0.5 µl.

The following protocol was used:
1) NCI-H460 cells were grown in Ham's F12 media supplemented with 10% FBS.
2) Cells were harvested and seeded into 96-well plates at 500 cells/well.
3) Peptides were diluted from DMSO stock solutions in 9-point doubling dilutions from a top concentration of 500 µM. Final DMSO concentration was constant at 1% (v/v).
4) In line with the supplied Nanocin-Pro protocol, diluted peptides were incubated with Nanocin-Pro in media for 20 minutes prior to addition to cells. Nanocin-Pro was used at a final assay concentrations of 0.2 µl/well.
5) Cells were grown in the presence of peptide for 96 hours at 37° C., 5% $CO_2$ in a humidified atmosphere.

6) After 96 h, Alamar blue 10% (v/v) was added, incubated for a further 4 h and fluorescent product detected using a BMG FLUOstar plate reader.

7) Media only background readings were subtracted before data was analysed using a 4-parameter logistic equation in GraphPad Prism.

HILRa-025 showed an LD$_{50}$ of −4.7 M against NCI-460, in medium alone and −6.5 M in the presence of Nanocin 2 μl. The concentration of Nanocin-Pro used, reduced cell viability by 36% in DMSO control wells compared to control wells in the absence of Nanocin-Pro. No peptide precipitation was observed for any peptides.

The results in FIG. 1 show that Nanocin Pro™ enhances the cytotoxicity of peptide Hilra-025, a cyclic peptide composed of a 'warhead' and 'backbone' as described in WO/2016/020437. This indicates that the potency of previously described cyclic peptides (for example those disclosed in WO12016/020437) which are not, alone, potent enough to be used in the clinic, have the potential of much higher specific activity if they could be better internalised.

HILRa-025 peptide without Dac incorporated showed auto-fluorescent properties above concentrations of 10 μM. The auto-fluorescent signal was predominantly located in the nucleus (data not shown). At lower concentrations of HILRa-025-Dac and CNTRL-Dac (6 μM in the absence of Nanocin-Pro, or 3 μM in the presence of Nanocin-Pro), clear imaging of DAC-peptide within the cell was achieved. The distribution was distinctly different to that seen at higher concentrations; being throughout the nucleus and cytoplasm, and showing a punctate appearance particularly in the cytoplasm (FIG. 4). Compared to controls treated with DMSO, cells treated with HILRa peptide had an appearance consistent with a state of autophagy. The punctate cytoplasmic localisation of DAC-peptide appeared to co-localise with autophagic vesicles. HILRa-025-DAC and CNTRL-DAC showed indistinguishable patterns of distribution within the cell. The presence or absence of Nanocin-PRO also did not cause a noticeable change in peptide localisation.

Example 2: Cyclisation of Linear Peptides Using CLIPS Technology

Synthesis and biological testing of peptides described herein was carried out by commercial research companies:

Peptide cyclisation was via the CLIPS method synthesised commercially by PEPSCAN PRESTO Zuiderslusveg 2, 8243 RC LELYSTAD, PO Box 2098, 8203 AB LELYSTAD Biological assays were carried out by: HORIZON DISCOVERY SERVICES, 8100 CAMBRIDGE RESEARCH PARK, UNITED KINGDOM, CB25 9TL Earlier experiments (Warenius et al, 2011 Selective anti-cancer activity of a hexapeptide with sequence homology to a non-kinase domain of Cyclin Dependent Kinase 4. Mol Cancer. 2011; 10: 72-88) in which the warhead was combined in a cyclic cassette with an amphiphilic polymer produced optimal results when the number of residues in the cassette was close to fifteen. This suggests that conformational constraint is likely to play a part in the activity of the warhead.

As an expert in constrained peptides, Pepscan has developed a proprietary, highly versatile constraining technology, called CLIPS (Chemical Linkage of Peptides onto Scaffolds; WO2004/077062). CLIPS technology involves the cyclization of linear peptides via reaction of thiol-functionalities of the cysteines with a small rigid entity. This anchor reacts exclusively with thiols and attaches to the peptide via covalent bonds. The CLIPS cyclization technology is unique for its versatility and ease of application. The cyclization reaction lasts no longer than 30 min, runs at room temperature and does not require any sort of catalysis.

The inventor undertook testing of the effect of various peptides which were cyclised using CLIPS technology on the killing of human non-small cell lung cancer cells (NCIH-460) in vitro. For each of the peptides, between two and four isomer fractions were received, giving a total of 12 peptide entities tested.

The following warhead lengths, obtained by adding flanking sarcosine residues, were tested:

TABLE 1

Optimising Length of Warhead-including Linear Peptide for CLIPS

| Peptide | Sequence | % inhibition at 1 mM | |
|---|---|---|---|
| | | 0.2 μl Nanocin-PRO per well | No Nanocin-PRO |
| HILRa-CL-01 | Ac-CPRGPRPC-NH2 | 12.9 | 0.0 |
| HILRa-CL-02 | Ac-C[Sar]PRGPRP[Sar]C-NH2 | 2.0 | 0.0 |
| HILRa-CL-03 | Ac-C[Sar][Sar]PRGPRP[Sar][Sar]C-NH2 | 9.5 | 0.0 |
| HILRa-CL-04 | Ac-CPKGPRPC-NH2 | 8.5 | 0.0 |
| HILRa-CL-05 | Ac-C[Sar]PKGPRP[Sar]C-NH2 | 1.1 | 0.0 |
| HILRa-CL-06 | Ac-C[Sar][Sar]PKGPRP[Sar][Sar]C-NH2 | 6.1 | 0.0 |
| HILRa-CL-07 | Ac-CPRGPKPC-NH2 | 1.5 | 0.0 |
| HILRa-CL-08 | Ac-C[Sar]PRGPKP[Sar]C-NH2 | 3.2 | 0.0 |

TABLE 1-continued

Optimising Length of Warhead-including Linear Peptide for CLIPS

| | | % inhibition at 1 mM | |
| | | 0.2 µl Nanocin-PRO per well | No Nanocin-PRO |
| Peptide | Sequence | | |
| --- | --- | --- | --- |
| HILRa-CL-09 | Ac-C[Sar][Sar]PRGPKP[Sar][Sar]C-NH2 | 3.0 | 1.1 |
| HILRa-CL-10 | Ac-CPKGPKPC-NH2 | 0.8 | 2.2 |
| HILRa-CL-11 | Ac-C[Sar]PKGPKP[Sar]C-NH2 | 1.2 | 0.0 |
| HILRa-CL-12 | Ac-C[Sar][Sar]PKGPKP[Sar][Sar]C-NH2 | 0.8 | 0.0 |
| Paclitaxel | — | $IC_{50}$ = 7.4 nM | — |

Although the 'clipped' linear peptides all showed very low killing of human non-small cell lung cancer in vitro at a concentration of 1 mM, using Nanocin Pro™ it was still possible to see that HILRa-CL-01 [Ac-(Pro-Arg-Gly-Pro-Arg-Pro)-NH2] was the optimal pre-clipped linear peptide warhead length (6 amino acids) when flanked by a cysteine residue at both the N- and C-termini. Interestingly, other 6 amino acid warheads (HILRa-CL-04, HILRa-CL-7 and HILRa-CL-10) in which the arginine residues at positions 2 and 5 were modified, showed varying activities. This data indicates that an arginine residue is required at least at position 5 in order to exert some cell killing effect. Substituting both anionic arginines by cationic homocysteic acids completely removed the cell killing effect (see for example HILRa-CL-16 A, B and C in FIG. 2). The data obtained also surprisingly indicates that an optimum warhead length of 6 amino acids results in optimal cancer cell cytotoxicity.

Example 3: Modification of Warhead Sequences

Using Nanocin Pro™, the 'clipped' Pro-Arg-Gly-Pro-Arg-Pro warhead could be demonstrated to cause just over 10% lethality of human non-small cell lung cancer cells at the very high concentration of 1.0 mM (see table 1).

$IC_{50}$ values obtained and % inhibition at the top concentration used in the assay (300 NM) are shown in the table below. Values in brackets are approximate due to extrapolated or incomplete dose response curves.

Cumulative experience from past experiments underlined the role of the two charged amino acids in cytotoxic activity but these charged groups gave the molecule a hydrophilicity that was likely to impair cell uptake and bind poorly in a putative hydrophobic binding site. All amino acids in the Pro-Arg-Gly-Pro-Arg-Pro site except the arginines were thus replaced by highly non-polar residues, chosen from a range of non-naturally occurring peptide molecules likely to provide resistance to peptidolysis.

To ascertain whether anionic groups could act in the warhead in a similar way to the cationic guanidium groups of the arginines, homocysteic acids were substituted at the arginine sites. The HILRa peptides were synthesised by standard automated peptide-synthesis using both normal and unusual amino acid precursors:

Dac=(Fmoc-β-(7-methoxy-coumarin-4-yl)-Ala-OH B-37407) BACHEM

Hca=Homocysteic acid Fmoc-4-(neopentyloxysulfonyl)-Abu-OH (S)-2-(Fmoc-amino)-4-neopentyloxysulfonyl-butyric acid. CAS 220951-81-5 Santa Cruz Biotechnology Inc Sar=Sarcosine (Fmoc precursor widely available commercially)

Nap=Naphthalene Fmoc-(R,S)-3-amino-3-(2-Naphthyl)pro-pionic acid CAS NO 269078-81-1 Santa Cruz Biotechnology Inc.

dmPro=dimethyl proline (R,S)-Boc-3,3-dimethyl-proline CAS No 143979-40-2 Polypeptide.com The following protocol was used:

1) NCI-H460 cells were grown in Ham's F12 media supplemented with 10% FBS.

2) Cells were harvested and seeded into 96-well plates at 500 cells per well.

3) Peptides were diluted 1:2 from DMSO stock solutions to generate a 9-point dose range from a top concentration of 300 µM. Final DMSO concentration was constant at 1% (v/v).

4) In line with the supplied Nanocin-PRO protocol, diluted peptides were incubated with Nanocin-PRO in media for 20 minutes prior to addition to cells. Nanocin-PRO was used at a final assay concentration of 0.2 µl per well.

5) Cells were grown in the presence of peptide for 96 hours at 37° C., 5% $CO_2$ in a humidified atmosphere.

6) After 96 h, Alamar blue 10% (v/v) was added, incubated for a further 4 h and fluorescent product detected using a BMG FLUOstar plate reader.

7) Media only background readings were subtracted before data was analysed using a 4-parameter logistic equation in GraphPad Prism.

The naphthalene precursor in the automated peptide synthesis used here, was Fmoc-(R,S)-3-amino-3-(2-Naphthyl) propionic acid) which is a mixture of sterereoisomers. Thus, after synthesis, purification and 'clipping' of the novel peptides each of the 4 warheads (as shown in Table 2 below) presented a mixture of stereoisomers (A, B and C) which were selectively purified and tested individually.

Viability assays of the CLIP cyclised peptides were performed to examine the effect of four HILRa clipped peptides on the viability of NCIH460 cells (up to three isomers for each of the peptides). Six isomers had no cytotoxic effect (data not shown). Results for HILRa 16A, 16B, 16C and HILRa 17A, 17B and 17C are depicted in FIG. 2.

As shown in Table 2 and FIG. 2, HILRa-CL-14 A, B and 16 A, B, C which contained homocysteic acid (Hca) had low detectable cancer cell-necrotic activity. Only the arginine-containing warheads HILRa-CL-15 A, B, C (SEQ ID No:6) and HILRA-CL-17 A, B, C (SEQ ID No:7) showed strong cytotoxic activity.

Assays were performed in the presence and absence of the peptide transfection reagent Nanocin-PRO. HILRa-CL-14 and HILRa-CL-16 (all isomers) showed negligible activity against NCIH460 cells. HILRa-CL-15 and HILRa-CL17 (all isomers) showed activity in the assay, with HILRa-CL-17 showing greater potency than HILRa-CL-15, and both peptides exhibiting greater potency in the presence of Nanocin-PRO. The presence of Nanocin-PRO reduced cell viability by 29% in DMSO control wells compared to control wells in the absence of Nanocin-PRO.

The following protocol was used:
1) NCI-H460 cells were grown in Ham's F12 media supplemented with 10% FBS.
2) Cells were harvested and seeded into 96-well plates at 500 cells per well.
3) HILRa peptides were diluted 1:2 from DMSO stock solutions to generate a 9-point dose range from a top concentration of 300 µM. Final DMSO concentration was constant at 1% (v/v).
4) In line with the supplied Nanocin-Pro protocol, diluted peptides were incubated with Nanocin-Pro in media for

TABLE 2

Cancer Cell Toxicity of Different Warhead Amino-acid Combinations

| Peptide or Compound | Peptide sequence | No Nanocin-PRO | | 0.2 µl Nanocin-PRO per well | |
| --- | --- | --- | --- | --- | --- |
| | | IC$_{50}$ | % inhibition at 300 µM | IC$_{50}$ | % inhibition at 300 µM |
| HILRa CL-14-A | Ac-CDacHcaSarProHcaNapC-NH2 | n/a | 10.5 | n/a | 9.9 |
| HILRa CL-14-B | | n/a | 5.8 | n/a | 6.8 |
| HILRa CL-15-A | Ac-C[Dac]R[Sar][dmPro]R[Nap]C-NH2 | n/a | 22.7 | 62.8 µM | 84.5 |
| HILRa CL-15-B | | n/a | 20.2 | 81.3 µM | 87.5 |
| HILRa CL-15-C | | n/a | 23.8 | 47.3 µM | 88.5 |
| HILRa CL-15-D | | n/a | 25.2 | 48.7 µM | 89.1 |
| HILRa CL-16-A | Ac-CDacHcaSarNapHcaNapC-NH2 | n/a | 9.9 | n/a | 0.0 |
| HILRa CL-16-B | | n/a | 14.1 | n/a | 0.0 |
| HILRa CL-16-C | | n/a | 26.9 | n/a | 0.5 |
| HILRa CL-17-A | Ac-C[Dac]R[Sar][Nap]R[Nap]C-NH2 | 213 µM | 90.3 | 5.38 µM | 98.7 |
| HILRa CL-17-B | | 130 µM | 99.2 | (2.10 µM) | 99.3 |
| HILRa CL-17-C | | 92.2 µM | 99.6 | (0.88 µM) | 99.4 |
| Paclitaxel | n/a | 4.95 nM | n/a | n/a | n/a |

Surprisingly, the substitution of dmPro in HILRa CL-15 with Nap in HILRa CL-17 resulted in a significant increase in inhibition which could not have been predicted. These experiments indicate that peptide warheads can have high cancer cell-necrotic activity which is dependent on the warhead sequence. The present inventor has surprisingly identified a number of peptide warheads which can be utilised to specifically target cancer cells for killing.

Example 4: NCI-H460 Cell Viability Assays Comparing the Effect of a Glycosylated Peptide (HILRa-Glu-01) and an Unglycosylated Peptide (HILRa-CL-17)

The inventor next undertook testing to determine whether the cytotoxicity of the peptides of the invention could be increased by glycosylation of the peptides. NCI-H460 cell viability assays were performed to compare the effect of a glycosylated clipped peptide (HILRa-Glu-01) versus the un-glycosylated version (HILRa-CL-17, HILRa-CL-17 was used in this study as a 1:1:1 mix of the three isomers HILRa-CL-17A, HILRa-CL-17B and HILRa-CL-17C).

Assays were performed in the presence and absence of the peptide transfection agent Nanocin-Pro.

20 minutes prior to addition to cells. Nanocin-Pro was used at a final assay concentration of 0.2 µl per well.
5) Cells were grown in the presence of peptide for 96 hours at 37° C., 5% CO2 in a humidified atmosphere.
6) After 96 h, Alamar blue 10% (v/v) was added, incubated for a further 4 h and fluorescent product detected using a BMG FLUOstar plate reader.
7) Media only background readings were subtracted before data was analysed using a 4-parameter logistic equation in GraphPad Prism.

The glycosylated peptide (HILRa-Glu-01) showed slightly lower activity in the assay compared to the un-glycosylated version (PRO CL-17) (FIG. 3). Both peptides showed much higher activity in the presence of Nanocin-PRO. The presence of Nanocin-Pro reduced cell viability in DMSO control wells by 16%.

It will be appreciated that numerous modifications to the above described peptides, pharmaceutical compositions, methods and uses may be made without departing from the scope of the invention as defined in the appended claims. For example, although in the example shown above the peptides showing very high cytotoxic activity have specific amino acid sequences, namely, Dac-Arg-Sar-dmPro-Arg-Nap and Dac-Arg-Sar-Nap-Arg-Nap, it will be appreciated that variations to these sequences can be made without departing from the scope of the invention as defined by the claims.

The invention claimed is:

1. A cyclic peptide comprising an active region which comprises the amino acid sequence $X^1X^2X^3X^4X^5X^6$ or a salt thereof, wherein:

$X^2$ and $X^5$ are arginine; and wherein:

$X^1$ is (7-methoxy-coumarin-4-yl)-Ala-OH (Dac), $X^3$ is any non-polar amino acid, and $X^4$ and $X^6$ are any non-polar amino acid selected from Dac, sarcosine (Sar), 3-amino-3-(2-naphthyl)propionic acid (Nap), and 5,5-dimethylproline (dmPro), wherein the active region is 6 to 10 amino acids in length.

2. The peptide according to claim 1 wherein $X^4$ and $X^6$ are Nap.

3. The peptide according to claim 1, wherein the active region of the peptide is between 6 and 8 amino acids in length.

4. The peptide according to claim 1 wherein the active region of the peptide comprises the amino acid sequence: Dac-Arg-Sar-dmPro-Arg-Nap (SEQ ID NO:4) or Dac-Arg-Sar-Nap-Arg-Nap (SEQ ID NO:5).

5. The peptide according to claim 1 wherein the active region of the peptide consists of the amino acid sequence: Dac-Arg-Sar-dmPro-Arg-Nap (SEQ ID NO:4) or Dac-Arg-Sar-Nap-Arg-Nap (SEQ ID NO:5).

6. The peptide according to claim 1, wherein the peptide comprises the amino acid sequence: $Y^1A^1X^1X^2X^3X^4X^5X^6A^2Y^2$ or a salt thereof, wherein:

A$^1$ and A$^2$ may be present or absent, wherein when A$^1$ and A$^2$ are present they comprise one or more amino acids; and Y$^1$ and Y$^2$ are cysteine.

7. The peptide according to claim 1 wherein the peptide comprises the amino acid sequence Cys-Dac-Arg-Sar-dm-Pro-Arg-Nap-Cys (SEQ ID NO:6) or Cys-Dac-Arg-Sar-Nap-Arg-Nap-Cys (SEQ ID NO:7).

8. The peptide according to claim 1 wherein the peptide consists of the amino acid sequence Cys-Dac-Arg-Sar-dm-Pro-Arg-Nap-Cys (SEQ ID NO:6) or Cys-Dac-Arg-Sar-Nap-Arg-Nap-Cys (SEQ ID NO:7).

9. The peptide according to claim 6 wherein the peptide is cyclised by reacting two thiol groups in the N- and C-terminal cysteine residues with a di-benzyl bromide linker.

10. A pharmaceutical composition comprising the peptide of claim 1 and a pharmaceutical acceptable carrier, diluent or excipient.

11. The pharmaceutical composition of claim 10 wherein the composition comprises a further therapeutic agent.

12. A method of treating non-small cell lung cancer comprising contacting a subject with the peptide of claim 1 or pharmaceutically acceptable salt thereof, wherein the non-small cell lung cancer cells are killed or their growth inhibited.

13. The method of claim 12, wherein the peptide or pharmaceutically acceptable salt thereof is administered with a further therapeutic agent.

14. The method of claim 12, wherein the subject is further treated with radiation therapy and/or surgery.

* * * * *